(12) United States Patent
Thramann

(10) Patent No.: US 9,039,753 B2
(45) Date of Patent: May 26, 2015

(54) SYSTEM AND METHOD TO ELECTRICALLY CHARGE IMPLANTABLE DEVICES

(71) Applicant: Jeff Thramann, Longmont, CO (US)

(72) Inventor: Jeff Thramann, Longmont, CO (US)

(*) Notice: Subject to any disclaimer, the term of this patent is extended or adjusted under 35 U.S.C. 154(b) by 0 days.

(21) Appl. No.: 14/019,324

(22) Filed: Sep. 5, 2013

(65) Prior Publication Data

US 2014/0067040 A1    Mar. 6, 2014

Related U.S. Application Data

(60) Provisional application No. 61/697,030, filed on Sep. 5, 2012.

(51) Int. Cl.
| | | |
|---|---|---|
| *A61F 2/06* | (2013.01) | |
| *A61N 1/00* | (2006.01) | |
| *A61N 1/378* | (2006.01) | |
| *A61F 2/82* | (2013.01) | |
| *A61F 2/07* | (2013.01) | |
| *A61N 1/20* | (2006.01) | |
| *A61L 31/14* | (2006.01) | |
| *A61F 2/00* | (2006.01) | |

(52) U.S. Cl.
CPC . *A61N 1/378* (2013.01); *A61F 2/82* (2013.01); *A61F 2/07* (2013.01); *A61F 2002/009* (2013.01); *A61F 2250/0001* (2013.01); *A61F 2250/0043* (2013.01); *A61N 1/205* (2013.01); *A61L 31/14* (2013.01)

(58) Field of Classification Search
CPC ..................................................... A61N 1/3785
USPC .............................. 607/35, 36; 623/1.18, 1.32
See application file for complete search history.

(56) References Cited

U.S. PATENT DOCUMENTS

| | | | |
|---|---|---|---|
| 7,167,746 B2 | 1/2007 | Pederson | |
| 7,235,098 B2 | 6/2007 | Palmaz | |
| 7,410,497 B2 | 8/2008 | Hastings et al. | |
| 7,898,096 B1 | 3/2011 | Krupenkin | |
| 2005/0177223 A1 | 8/2005 | Palmaz | |
| 2006/0052744 A1 | 3/2006 | Weber | |
| 2006/0089709 A1 | 4/2006 | Helmus | |
| 2006/0106451 A1 | 5/2006 | Busiashvili | |

(Continued)

OTHER PUBLICATIONS

International Search Report and Written Opinion of the International Searching Authority for PCT/US2013/058304, mailed Dec. 18, 2013. 12 pages.

(Continued)

*Primary Examiner* — Thomas J Sweet
*Assistant Examiner* — Brian Dukert
(74) *Attorney, Agent, or Firm* — Perkins Coie LLP

(57) ABSTRACT

An implantable device having a power source is provided. The power source uses reverse electrowetting technology to generate a charge to power the implantable device. The power source includes a flexible, non-conductive substrate having a first side and a second side opposite the first side with a channel between the first and second sides. Electrodes are arranged about the channel in a predefined pattern. A liquid is contained in the channel. The liquid includes a dielectric liquid and a conductive liquid that do not mix. The electric change is generated by moving the liquid back and forth across the electrodes. The force to pump or move the liquid is provided by organic means, such as, for example, the change in blood pressure between systolic and diastolic, the expansion and contraction of an organ, or the movement of a muscle.

14 Claims, 7 Drawing Sheets

(56) References Cited

U.S. PATENT DOCUMENTS

| | | |
|---|---|---|
| 2007/0150009 A1 | 6/2007 | Kveen et al. |
| 2007/0244536 A1 | 10/2007 | Pederson |
| 2008/0215117 A1 | 9/2008 | Gross |
| 2009/0036975 A1 | 2/2009 | Ward et al. |
| 2010/0045048 A1* | 2/2010 | Pless ............................ 290/1 R |
| 2011/0109203 A1 | 5/2011 | McAlpine et al. |
| 2011/0180886 A1 | 7/2011 | El Rifai et al. |
| 2012/0312456 A1 | 12/2012 | McAlpine et al. |

OTHER PUBLICATIONS

Boudway, I. "Tom Krupenkin's Power Shoes" Bloomberg BusinessWeek Magazine. Dec. 1, 2011; Retrieved from <http://www.businessweek.com/magazine/tom-krupenkins-power-shoes-12012011.html> on Dec. 12, 2013. 2 pages.

Bourzac, K. "Innovators Under 35: Michael McAlpine, 32" MIT Technology Review. Accessed from <http://www2.technologyreview.com/TR35/Profile.aspx?TRID=951> on Dec. 3, 2013. 2 pages.

Krupenkin, T. and Taylor, A. "Reverse electrowetting as a new approach to high-power energy harvesting." Nature Communications 2:448. Published Aug. 23, 2011. 7 pages.

Vilares, R. et al. "Flexible and biocompatible polymer microfluidic devices with integrated electrodes based on a CMOS compatible technology." Ikerlan S. Coop. MEMS/MST Department. Sep. 17, 2006. 1 page.

\* cited by examiner

SYSTEM AND METHOD TO ELECTRICALLY CHARGE IMPLANTABLE DEVICES

CLAIM OF PRIORITY UNDER 35 U.S.C. §119

The present application claims priority to U.S. Provisional Patent Application Ser. No. 61/697,030, filed Sep. 5, 2012, the disclosure of which is incorporated herein by reference as if set out in full.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates generally to electrically charging devices implantable into animals, and more specifically, to using differential pressures generated by muscles, organs, and other tissue to electrically charge an implantable device.

2. Background

Vascular stents and other devices that are implantable into animals, such as people or the like, are used frequently to treat a medical condition. For example, a stent may be used to remove an aneurysm from direct contact with blood flow or the like. In another example, a pacemaker may be implanted to treat abnormal heart rhythms. In still other examples, electrical stimulators may be used stimulate and treat muscles or nerves, including such nerves as optical nerves, spinal nerves, and peripheral nerves.

Many of the implantable devices suffer from one drawback or another. Implantable devices that require electrical energy, such as pacemakers or stimulators, require a battery in most instances. Eventually the battery is drained and must be replaced or recharged prior to the implantable device ceasing to operate as required to treat the condition.

Stents, as mentioned, are effective in treating certain coronary and vascular diseases and conditions. Stents may facilitate or even cause the formation of thrombosis or clots once placed in the blood vessels. The clots may cause blockage or decreased blood flow that may lead to a stroke or heart attack.

One solution to the formation of clots is to provide stents with anticoagulation pharmacologic agents (a.k.a. drugs). The anticoagulation drug, such as Heparin, is typically loaded in or coated on the stent. The medication is released from the stent over time and inhibits the formation of clots. While an improvement over a bare metal stent or the like, medicated, or eluting, stents still suffer from drawbacks.

It has been discovered that the formation of clots on stents may be inhibited by providing a negative charge on the stent. In one solution, the negative charge on the stent is provided by implanting a battery along with the stent, which has the problems mentioned above.

Thus, against the above background an improved system and method to electrically charge implantable devices is needed and, more particularly, an improved system and method to negatively charge a stent to inhibit clotting.

SUMMARY

Embodiments disclosed herein address the above stated needs by providing an implantable device with an implantable power supply. The implantable power supply converting mechanical energy of the body, such as the expansion and contraction of muscles into electrical energy using microfluidics or mechanical strain.

DETAILED DESCRIPTION

The technology of the present patent application will now be explained with reference to various figures, tables, and the like. While the technology of the present application is described with respect to certain devices implantable in animals, such as, vascular stents, pacemakers, and an electrical stimulation device, one of ordinary skill in the art would now recognize that the technology is applicable to other implantable devices that may require a charge or a power source. Additionally, the technology of the present application may be presented in reference to people; however, one of ordinary skill in the art on reading the disclosure contained herein will now understand that the technology may be usable in other animals, both wild and domestic. Moreover, the technology of the present patent application will be described with reference to certain exemplary embodiments herein. The word "exemplary" is used herein to mean "serving as an example, instance, or illustration." Any embodiment described herein as "exemplary" is not necessarily to be construed as preferred or advantageous over other embodiments absent a specific indication that such an embodiment is preferred or advantageous over other embodiments. Additionally, in certain instances, only a single "exemplary" embodiment is provided. A single example is not necessarily to be construed as the only embodiment. The detailed description includes specific details for the purpose of providing a thorough understanding of the technology of the present patent application. However, on reading the disclosure, it will be apparent to those skilled in the art that the technology of the present patent application may be practiced with or without these specific details. In some descriptions herein, generally understood structures and devices may be shown in block diagrams to aid in understanding the technology of the present patent application without obscuring the technology herein. In certain instances and examples herein, the term "coupled" or "in communication with" means connected using either a direct link or indirect data link as is generally understood in the art. Moreover, the connections may be wired or wireless, private or public networks, or the like.

Figure 1:
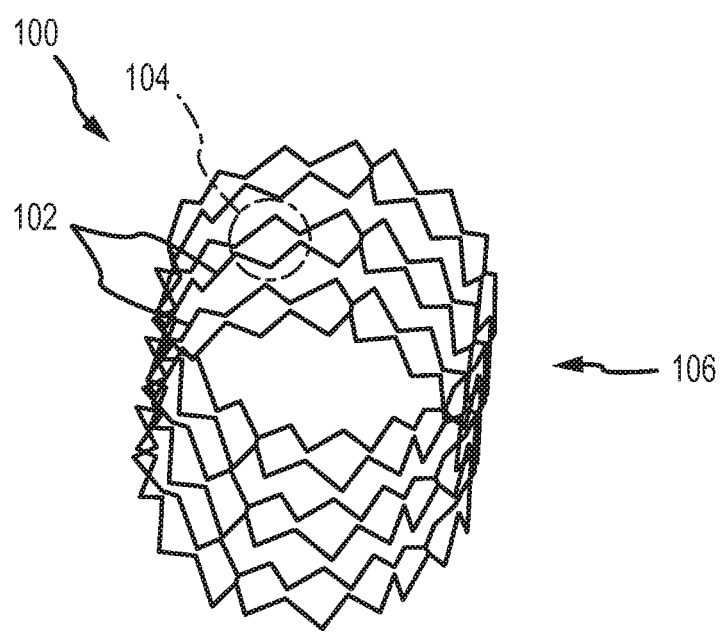
FIG. 1 is a perspective view of a bare metal stent consistent with the technology of the present application.
Figure 2A:
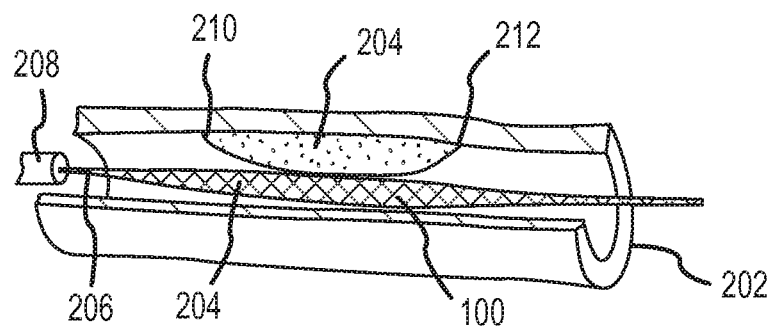
FIG. 2A-2C is a cutaway series of figures showing the implantation of the bare metal stent and expansion of the stent from a collapsed to an expanded state.
Figure 2B:
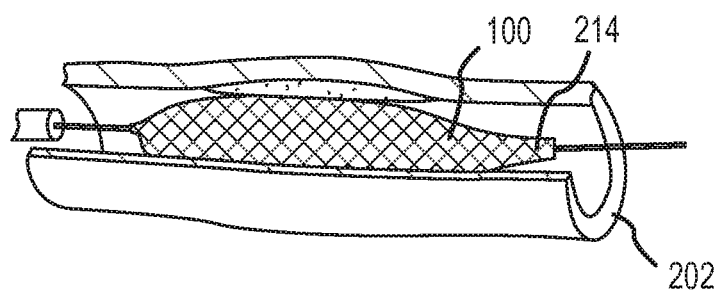
Figure 2C:
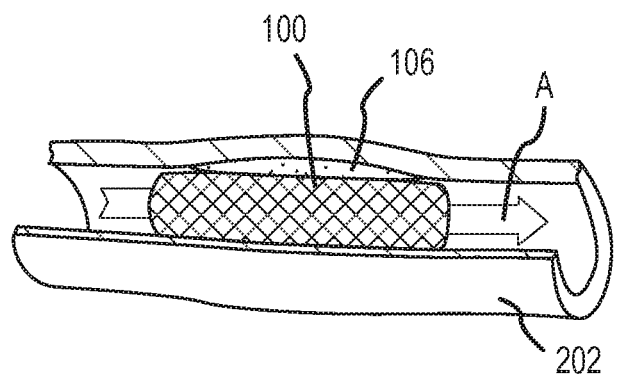

Referring first to FIG. 1, a stent 100 is shown. Stent 100 may generally be referred to as a bare metal stent. Stent 100 is formed of a number of interconnected metallic members 102 that form expandable structures 104 that may be elongated and compressed or expanded, as shown in expanded state 106. As is generally known in the art, stent 100 may be loaded with pharmacological agents and/or covered with a flexible material, such as a flexible metal or polymer. With further reference to FIGS. 2A-2C, a cutaway of an artery 202 having a partial blockage 204, which may be plaque or the like, is shown. The stent 100 in a collapsed state 204 is delivered to the portion of the vascular anatomy via a catheter 206 and lumen 208 delivery mechanisms. The stent 100 is placed in the artery 202 such that the stent 100 extends from a proximal side 210 to a distal side 212 of the blockage. As shown in FIG. 2B, an expansion device 214, such as a balloon as shown, is provided on the catheter 206 to expand the stent 100 from the collapsed state 204 to an expanded state 106, as shown in FIG. 2C. The expansion device 214, catheter 206, and lumen 208 are removed to allow blood flow through the artery 202 as shown by arrow A. One of ordinary skill in the art would recognize on reading the disclosure that the stent 100 may be deployed in numerous locations throughout the vascular system.

Figure 3:
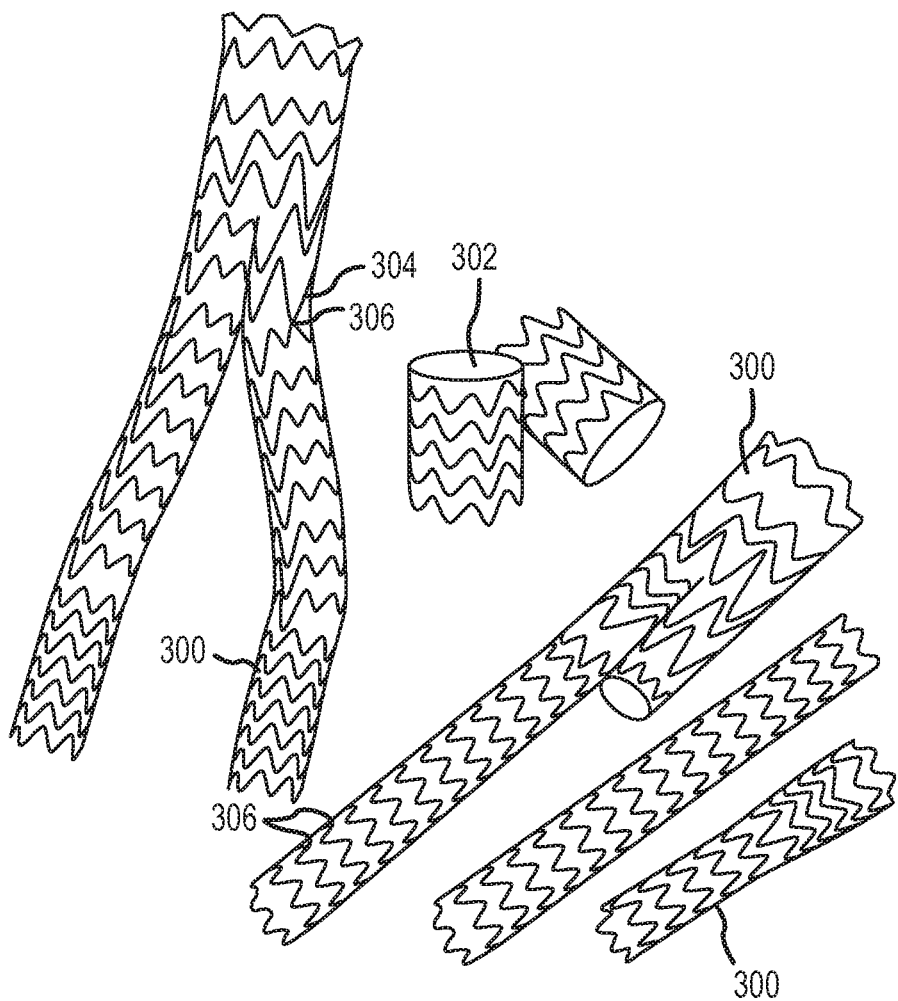
FIG. 3 is a view of a stent graft consistent with the technology of the present application.

The bare metal stent 100 is typically associated with a coronary artery and blockage. With reference to FIG. 3, a stent graft 300 is shown in multiple configurations. The stent graft 300 typically comprises a fabric 302 supported by a rigid structure 304. The fabric 302 is elastic and the rigid structure 304 has bends 306 to allow the rigid structure 304 to straighten as the stent graft 300 is expanded. The stent graft 300 may be used in endovascular repair procedures, such as, for example, an aneurysm repair.

As described above, stent 100 and stent graft 300 may develop blood clots that may lead to blockage in the vascular system resulting in a heart attack, stroke, or the like. As described above, blood clot formation may be inhibited by negatively charging the stent 100 or the stent graft 300. Heretofore, a battery may be provided directly connected to the stent or electromechanically connected to the stent, see for example, United States Published Patent Application Publication No. 2006/0106451, the disclosure of which is incorporated herein as if set out in full. Using an independent battery adds the difficulty of (1) implanting the battery, (2) connecting the battery to the stent, (3) the life of the battery to name but three difficulties.

A piezoelectric material develops charge or electrical energy in response to applied mechanical stress. Piezoelectricity or the piezoelectric effect is a linear electrometrical interaction between the mechanical and the electrical states in certain materials. Placing a strain on the piezoelectric material causes the generation of a charge. The reverse piezoelectric effect is by applying a charge to the material similarly causeing a mechanical strain.

Figure 4:
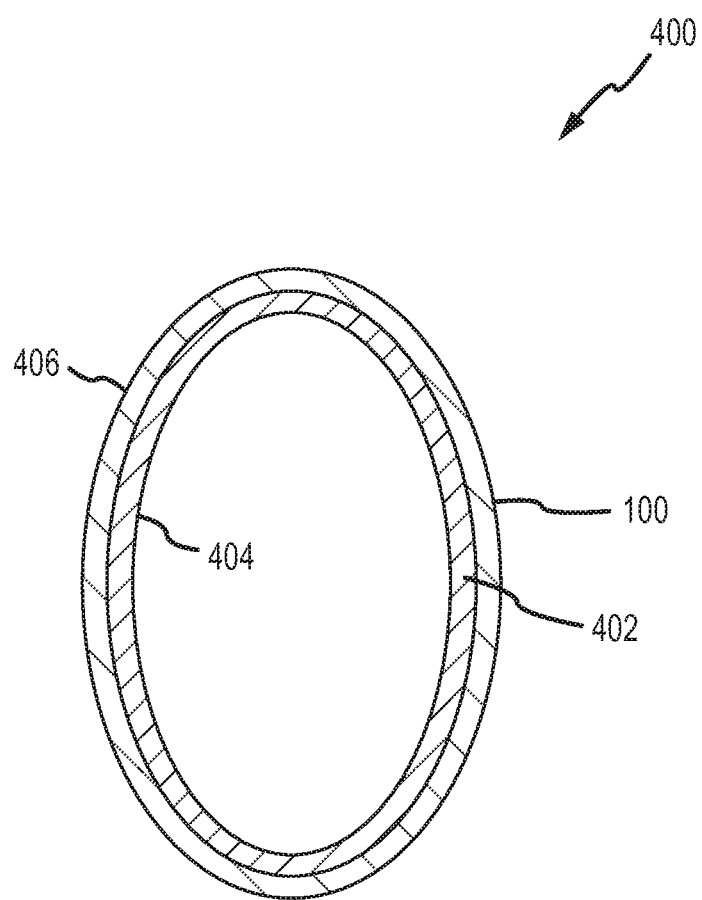
FIG. 4 is a cross section of a stent or stent graft of FIGS. 1 and 3 consistent with the technology of the present application.

Certain polymers develop electrical charges under strain. The piezoelectricity effect generally relates to placing a strain on the polymers when the polymers are flexed or stretched. One exemplary type of stretchable polymer is a polyvinylidene fluoride (PVDF). With reference to FIG. 4, a cross section of a charge generating stent 400 is provided. Charge generating stent 400 may be either a bare metal stent 100 or a stent graft 300 as explained above. If stent 400 includes a bare metal stent 100, as shown, a flexible layer of a piezoelectric polymer 402 is provided. If stent 400 is a stent graft 300, the fabric 302 may be replaced by the piezoelectric polymer 402 or, in certain embodiments, the piezoelectric polymer 402 is layered on the fabric 302. In either case, the piezoelectric polymer 402 is provided on the stent 400 in such a way as to provide a negative charge on the interior layer 404 as it has been found that the negative charge on the interior layer of the stent 400 inhibits the formation of clots and the like. As a corollary, the outer layer 406 may be provided with a positive charge relative to the internal layer as compared to the inner layer of stent 400. The charge on the piezoelectric polymer 402 is generated by the blood pressure expanding and contracting the blood vessels, including the stent 400. The expansion and contraction generates strain on the piezoelectric polymer 402 that in turn generates the negative charge on the interior layer 404 of the stent 400.

Figure 5:
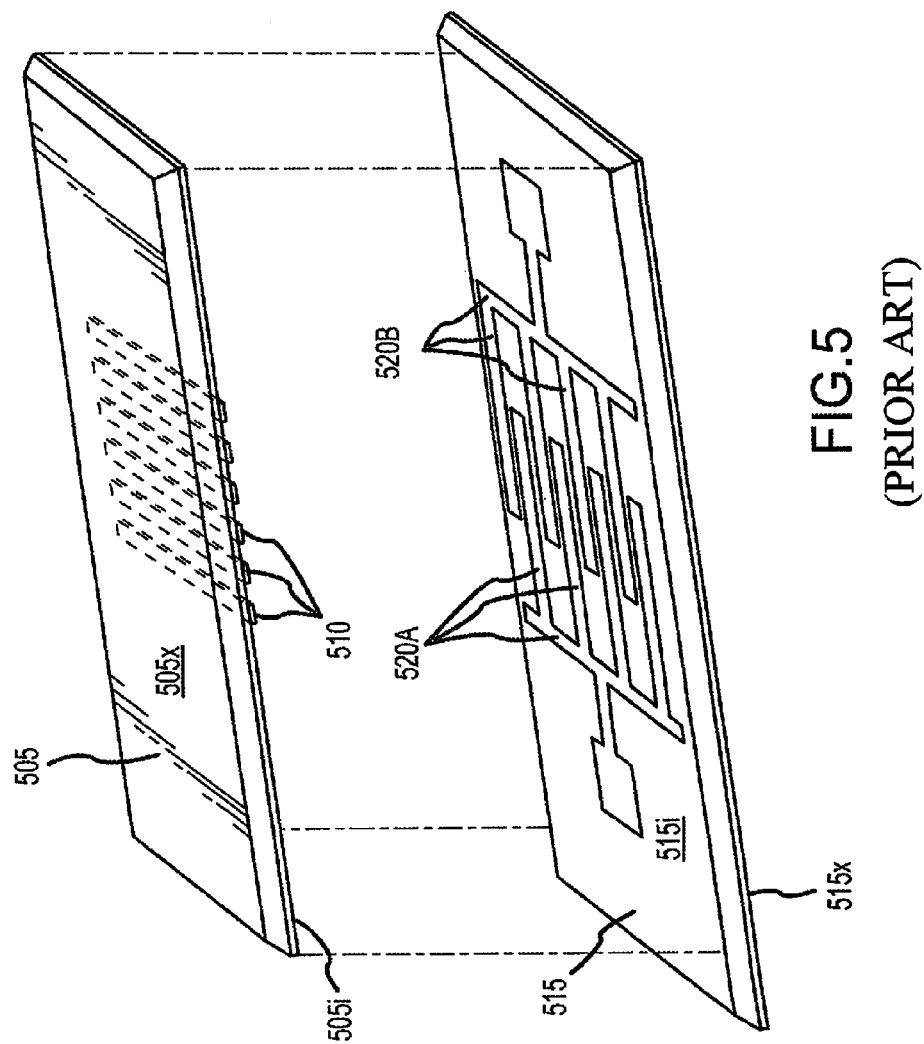
FIG. 5 is an exploded view of a piezoelectric material usable with the stent or stent graft of FIGS. 1 and 3.

PVDF has a number of drawbacks that are generally known in the art. Thus, while it is possible to use PVDF to generate a negative charge on the interior layer of stent 400, alternative power sources are desirable. One promising material is a flexible piezoelectric structure disclosed in United States Published Patent Application Publication Number 2011/010923A1, filed Mar. 19, 2010, and incorporated herein by reference as if set out in full. In one embodiment, as shown in FIG. 5, the piezoelectric includes first and second flexible substrates 505, 515. For use with devices designed to be implanted to animals, the flexible substrates should be formed of biocompatible materials that are generally known in the art. The flexible substrates 505, 515 have an external side 505$x$, 515$x$ and an internal side 505$i$, 515$i$. A plurality of piezoelectric film strips 510 may be coupled to the internal side 505$i$ of one of the flexible substrates 505. Suitable piezoelectric film strips 510 may be constructed from crystalline piezoelectric materials such as, for example, lead zirconate titanate, zinc oxide, Quartz, and the like as are generally known in the art. Flexible conductive electrodes 520A and 520B may be coupled to the internal side 515$i$ of the other flexible substrate 515. The flexible conductive electrodes may be formed on flexible substrate 515 using any number of conventional depositing techniques. The plurality of piezoelectric film strips 510 form an electrical circuit across the electrodes 520A, 520B. In certain embodiments, the flexible substrates 505, 515 form a protective biocompatible capsule for the electrical circuit.

Figure 6:
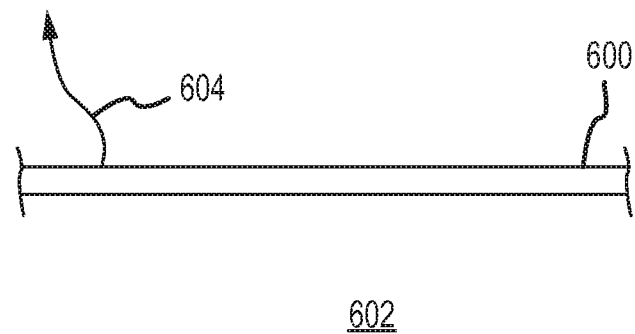
FIG. 6 is a block diagram of a stent or stent graft attachable to muscles, organs, or tissue consistent with the technology of the present application.

The flexible piezoelectric, shown in FIG. 5, provides an improvement in the generation of an electrical charge over the PVDF piezoelectric previously known. However, the generation of power by the piezoelectrics using differences in systolic and diastolic pressure is limited. Additional power may be provided if the flexible material was implanted into a muscle that has stronger expansion and contraction pressure or, alternatively, an organ. For example, larger strains may be implemented if the flexible piezoelectric is implanted into the lungs, the diaphragm, the heart, or other muscle, organs, or tissues that expand and contract. As shown in FIG. 6, a flexible piezoelectric 600 may be adapted for attachment to tissue 602, such as a muscle or organ. In certain instances, the muscle or organ may be the heart, the diaphragm or the lungs to name but three options. Leads 604 may extend from the electrodes, such as electrodes 520A, 520B above, to the implanted device that requires power. The leads may be coaxial style leads, twisted pair leads, or the like. The leads 604 may connect to a stent, such as stent 100, or a stent graft, such as stent graft 300 to provide a negative charge to the stent. In other embodiments, the leads 604 may supply a charge to rechargeable batteries, such as, for example, batteries associated with a pacemaker or a nerve stimulator to name two examples.

Figure 7:
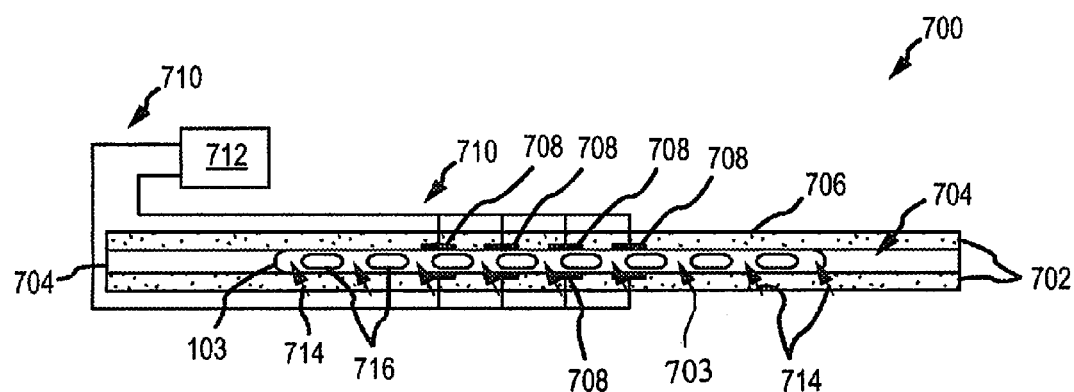
FIG. 7 is a cross sectional view of a microfluidic device capable of converting mechanical energy to electrical energy consistent with the technology of the present application.
Figure 8:
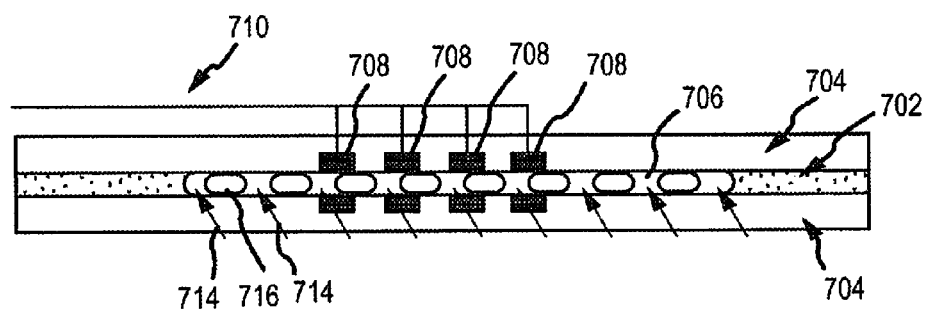
FIG. 8 is a plan view of the microfluidic device of FIG. 7.

While piezoelectric devices provide a useful source of electrical energy, the body has a limited ability to place strain on materials. Alternatively, it may be possible to use the expansion and contraction of organs, tissue, muscles, and the like, and/or the change in pressure of the vascular system to provide mechanical energy that is convertible to electrical energy using reverse electrowetting technologies. In other words, the reverse electrowetting structure explained herein is a means for generating an electrical charge to power, at least in part, implantable devices. The expansion, contraction, pressure differentials, or the like may be used to provide pumping action for microfluidic devices built into the implantable device, or separate from the implantable device and connected by electrical leads. One possible microfluidic device 700 is shown in FIGS. 7 and 8, and as disclosed in U.S. Pat. No. 7,898,096, which issued Mar. 1, 2011, and which is incorporated herein by reference as if set out in full. As shown in FIGS. 7 and 8, planar substrates 702 are provided separated by spacers 704 to form a channel 706 or space. Substrates 702 and spacers 704 should be formed of a dielectric or non-conductive material. A plurality of electrodes 708 are arranged about the channel 706. Leads 710 complete the electrical circuit to the implantable device 712, which may be a stent, pacemaker, stimulator, batteries, or the like. The microfluidic device 700 may directly power implantable devices or provide a continuous charge to prolong the life of the implantable device.

A movable fluidic body 703 is disposed in channel 706 and configured to slide along channel 706 past electrodes 708. Fluidic body 703 consists of two immiscible liquids, one being a dielectric liquid and the other one being an electrically conductive liquid. Examples of suitable electrically conductive liquids include aqueous salt solutions and molten salts. Exemplary aqueous salt solutions include 0.01 molar solutions of salts such as $CuSO_4$, $LiCl$, $KNO_3$, or $NaCl$. Exemplary molten salts include 1-ethyl-3-methylimidazolium tetrafluoroborate and 1-ethyl-3-methylimidazolium trifluoromethanesulfonate, which are both commercially available. In other cases, the conductive liquid can comprise liquid metals such as gallium, indium or mercury. Examples of suitable dielectric liquids include silicone oils and alkanes. Exemplary silicone oils include polydimethylsiloxane and polydiphenylsiloxane, and exemplary alkanes include nonane and heaxadecane.

Conductive and dielectric liquids are spatially separated in a plurality of distinct regions. Dielectric liquid regions 714 and conductive liquid regions 716 are arranged in a periodic alternating pattern, such that conductive and dielectric regions regularly alternate. The boundaries between immiscible liquid regions are preserved by the surface tension forces, giving fluidic body 703 an ability to move as a whole, e.g. slide along channel 706 without disturbing the arrangement and volume of the above-mentioned distinct liquid regions.

The pumping action to move the fluidic body 703 may be provided by the change between systolic and diastolic blood pressure, the expansion and contraction of muscles, the expansion and contraction of the lungs, or other tissues, organs, and the like. As the fluidic body 703 moves past the electrodes 708, the mechanical energy is converted into electrical energy to power or charge the implantable device 712.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. An electrically charged stent configured for implantation to a cardiovascular system, the stent comprising:
 a flexible material formed into an elongate tube, the flexible material including an inner surface and an outer surface;
 at least one channel residing in the flexible material between the inner and outer surfaces;
 at least two electrodes arranged on the at least one channel;
 a fluid contained in the at least one channel, the fluid comprising:
  a dielectric fluid; and
  a conductive fluid, wherein the dielectric fluid and conductive fluid are alternatingly arranged in the at least one channel,
 wherein the flexible material is configured to expand and contract and provide a motive force to oscillate the fluid in the at least one channel such that the dielectric fluid and conductive fluid move past the at least two electrodes and generate an electric charge;
 wherein the plurality of electrodes are coupled to the inner surface and the outer surface to provide an electrical charge to the stent; and
 wherein the plurality of electrodes are configured to alternatingly apply a negative charge and a positive charge to the inner surface of the electrically charged stent.

2. The electrically charged stent of claim 1 wherein the flexible material is configured to expand and contract based on a change of blood pressure between systolic and diastolic blood pressures.

3. The electrically charged stent of claim 1 wherein the plurality of electrodes are configured to negatively charge the inner surface of the electrically charged stent.

4. The electrically charged stent of claim 1 wherein the dielectric fluid and the conductive fluid are immiscible.

5. The electrically charged stent of claim 1 wherein the dielectric fluid comprises a first plurality of regions in the at least one channel and wherein the conductive fluid comprises a second plurality of regions in the at least one channel and wherein the first plurality of regions are spaced apart by the second plurality of regions over a length of the at least one channel.

6. An apparatus comprising:
 an implantable device comprising a charge generating stent configured for implantation to a body;
 a power source configured for implantation into the body and electrically coupled to the implantable device, the power source comprising:
  a flexible, non-conductive substrate having a first side and a second side opposite the first side;
  at least one channel contained in the flexible, non-conductive substrate between the first and second sides;

a plurality of electrode pairs arranged on opposite sides of the at least one channel and arranged in a predetermined pattern;

a liquid in the at least one channel, wherein the liquid comprises a plurality of dielectric regions and a plurality of conductive regions wherein each of the plurality of dielectric regions is formed by a dielectric liquid and each of the plurality of conductive regions is formed by a conductive liquid wherein the dielectric and the conductive liquids are immiscible, wherein force applied to the flexible, non-conductive substrate causes the liquid in the at least one channel to move such that the plurality of dielectric regions and the plurality of conductive regions move across at least one of the plurality of electrode pairs to generate an electrical charge to power at least in part the implantable device, wherein the plurality of electrodes are configured to alternatingly apply a negative charge and a positive charge to an inner surface of the charge generating stent.

7. The apparatus of claim 6 wherein the power source is integrated into the implantable device.

8. The apparatus of claim 6 wherein the power source is configured for implantation on an organ that expands and contracts wherein the expansion and contraction is the force applied to the flexible, non-conductive substrate.

9. The apparatus of claim 6 wherein the power source is configured for implantation on a muscle that expands and contracts wherein the expansion and contraction is the force applied to the flexible, non-conductive substrate.

10. An apparatus comprising:
   a charge generating stent configured for implantation to a body; and
   means for generating an electrical charge to power the implantable device electrically coupled to the implantable device, wherein the means or generating comprises a reverse electrowetting device having at least two electrodes coupled across the charge generating stent wherein the at least two electrodes are configured to alternatingly apply a negative charge and a positive charge to an inner surface of the charge generating stent.

11. The apparatus of claim 1 wherein the electrically charged stent is a bare metal stent.

12. The apparatus of claim 1 wherein the electrically charged stent is a stent graft.

13. The apparatus of claim 6 wherein the charge generating stent is a bare metal stent.

14. The apparatus of claim 6 wherein the charge generating stent is a stent graft.

* * * * *